(12) United States Patent
Cecchi

(10) Patent No.: US 7,114,966 B2
(45) Date of Patent: Oct. 3, 2006

(54) APPARATUS FOR A QUICK RELEASE SAFETY CONNECTOR ASSEMBLY

(75) Inventor: Marino Cecchi, Lake Geneva, WI (US)

(73) Assignee: Thomson Licensing, Boulogne-Billancourt (FR)

( * ) Notice: Subject to any disclaimer, the term of this patent is extended or adjusted under 35 U.S.C. 154(b) by 0 days.

(21) Appl. No.: 10/477,798

(22) PCT Filed: May 13, 2002

(86) PCT No.: PCT/US02/15055

§ 371 (c)(1),
(2), (4) Date: Nov. 14, 2003

(87) PCT Pub. No.: WO03/005493

PCT Pub. Date: Jan. 16, 2003

(65) Prior Publication Data

US 2005/0014404 A1    Jan. 20, 2005

Related U.S. Application Data

(60) Provisional application No. 60/290,752, filed on May 14, 2001.

(51) Int. Cl.
*H01R 4/58* (2006.01)
(52) U.S. Cl. ........................................................ 439/88
(58) Field of Classification Search ................ 439/282, 439/281, 289, 607, 936, 89, 88, 931
See application file for complete search history.

(56) References Cited

U.S. PATENT DOCUMENTS

| | | | | |
|---|---|---|---|---|
| 3,850,495 A | * | 11/1974 | Glover | 439/273 |
| 3,953,099 A | * | 4/1976 | Wilson | 439/205 |
| 4,003,620 A | * | 1/1977 | O'Brien et al. | 439/204 |
| 4,240,466 A | | 12/1980 | Herzan et al. | 137/614 |
| 4,406,506 A | | 9/1983 | Baldwin | 339/36 |
| 4,433,206 A | * | 2/1984 | Lewis | 174/35 C |
| 4,477,136 A | | 10/1984 | Smith | |
| 4,609,247 A | * | 9/1986 | Annoot | 439/591 |
| 4,707,046 A | | 11/1987 | Strand | 439/314 |
| 5,431,578 A | | 7/1995 | Wayne | 439/259 |
| 5,432,916 A | * | 7/1995 | Hahn et al. | 710/302 |
| 5,509,823 A | | 4/1996 | Harting et al. | |
| 5,674,088 A | | 10/1997 | Roche et al. | 439/474 |
| 5,992,817 A | | 11/1999 | Klitsner et al. | 248/694 |

FOREIGN PATENT DOCUMENTS

| | | |
|---|---|---|
| EP | 334 609 B1 | 9/1989 |
| FR | 0 178 953 | 4/1986 |
| JP | 404206182 * | 7/1992 |

* cited by examiner

OTHER PUBLICATIONS

Robert Bosch, "Dispositif de connexion a emboitement, notamment pour conducteurs electriques", Demande le 1er mars 1965, a 15h 46m, Paris.

*Primary Examiner*—Phuong Dinh
(74) *Attorney, Agent, or Firm*—Joseph J. Laks; Ronald H. Kurdyla; Joel M. Fogelson

(57) ABSTRACT

An electrical connector assembly for providing quick and easy release of a mated plug in the event of unintentional physical interference with the plug and/or connector. The quick release safety connector is made of a resilient material for providing a secure yet flexible grip on the plug sufficient to maintain an electrical connection, while at the same time facilitating immediate and reliable release between connected devices in the event of accidental interference with the connecting cord and/or either of the connected devices.

19 Claims, 2 Drawing Sheets

APPARATUS FOR A QUICK RELEASE SAFETY CONNECTOR ASSEMBLY

This application claims benefit under 35 U.S.C. § 365 of International Application PCT/US02/15055 filed May 13, 2002, which claims the benefit of U.S. Patent Application No. 60/290,752 filed May 14, 2001.

FIELD OF INVENTION

The present invention relates to electrical connectors, and in particular to a two-part electrical connector capable of releasing a cable from a host device, with minimal separation force, if the cable or host device is physically interfered with.

BACKGROUND OF INVENTION

The electrical connections between devices (e.g., a computer and a peripheral device) are usually difficult to disconnect, i.e., it is difficult to separate most cables with connecting plugs from their corresponding sockets, unless intentionally designed to do so. Moreover, most computers, video game consoles, and other connectable host devices come with one or more Universal Serial Bus (USB) port connections. Peripheral devices (e.g., printers, scanners, modems, etc.) connect to USB ports of host devices through the use of USB connectors, but such connectors are difficult to separate from USB ports of host devices.

USB based ports and connectors are extensively used because a multitude of devices may be connected to a host device at the same time. This feature of USB connections presents a safety issue in the event of, for example, unintended physical movement that causes either a host or peripheral device to be dislocated due to an unexpected pulling of a connecting cord. Since it is unlikely that the pulled cord will disconnect from a port in the event of such an accident, bodily injury may result because the pulled cable could drag a connected host device off a shelf, striking a user or a bystander. Injury may also occur when a connecting cord becomes entangled around a user's toot or leg, as to trip that person. In addition, damage to the host and/or peripheral device, as well as to the connecting cable and/or connector itself can result during such accidents.

Accordingly, an easily installed electrical connector apparatus that provides a secure connection when connected to a host device and also affords a reliable quick release of a cord from connection to a host device in the event of an accident, due to unintentional disruption of the cord, is desirable.

SUMMARY OF INVENTION

The present invention is directed towards an electrical connector assembly comprising a connector having a socket end. The socket end is formed of a resilient material for flexibly securing a head end of a mating plug that is inserted into a socket cavity of the connector. The head end promptly disconnects from the socket cavity in the event of, for example, unintentional physical interference with a connecting cord.

BRIEF DESCRIPTION OF THE DRAWINGS

In the drawings, wherein like reference numerals denote similar elements throughout the views.

DETAILED DESCRIPTION OF THE DRAWINGS

Figure 1:
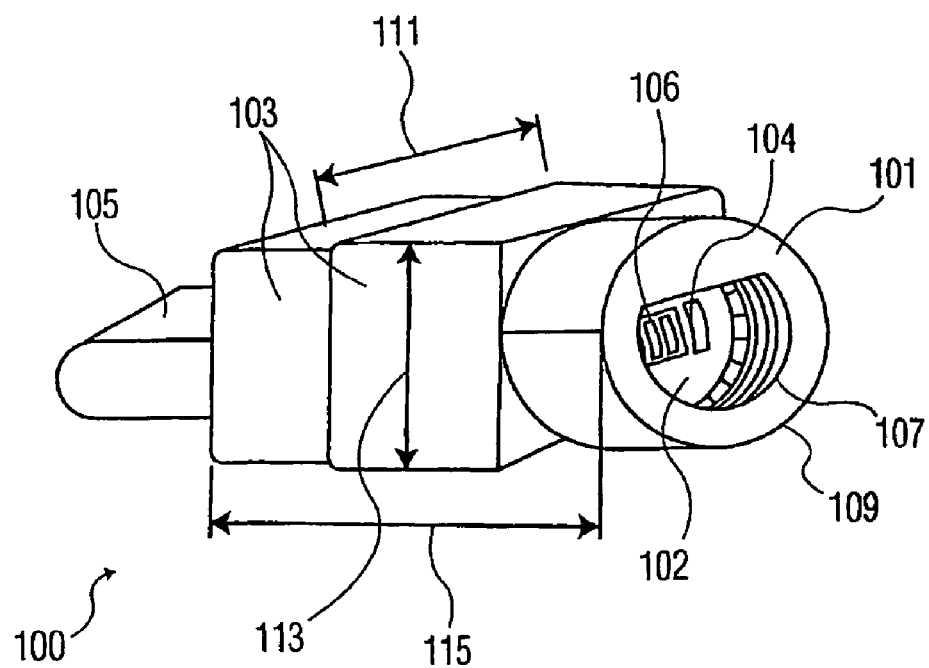
FIG. 1 is a perspective view of a safety connector according to an embodiment of the present invention.

Referring now to the Figures, FIG. 1 depicts an exemplary perspective view of safety connector 100 according to an aspect of the present invention. Safety connector 100, also referred to as connecting member, includes socket 101 attached to a first end of connector housing 103. Socket 101 is shown cylindrical in shape and is formed of a flexible and/or resilient material to allow for insertion and securing (appending) of mating plug 200 (see FIG. 2) within socket cavity 102 by way of, for example, resiliently pressing against a corresponding portion of mating plug 200. Socket 101 also allows for easy release of mating member 200 by virtue of its resiliency. Exemplary materials for the composition of socket 101 may be rubber (e.g., silicone rubber), vinyl, foam, plastic, or any other soft, flexible material.

Socket cavity 102 includes an opening passing laterally through socket 101 and is preferably of sufficient diameter, shape, and depth to securely yet flexibly receive head portion 201 of mating plug 200. In one embodiment, central portion of the socket cavity 102 has a width that is greater than either opening portion 309 or end portion 311 of socket cavity 102 (see FIG. 3A). In another embodiment, the face of socket cavity 102 comprises a substantially semi-circular shape.

Socket cavity 102 includes a plurality of contacts, for example, connector outer pins 104 and connector center pin assembly 106. In one embodiment, connector outer pins 104 may comprise, for example, pins for providing power and grounding, while the connector center pin assembly 106 may comprise, for example, a plurality of data transmission pins. In an alternative embodiment, outer pins 104 are for data transmission and center pins assembly 106 provides power.

In accordance with one embodiment, external connector 105 can be formed to the second end of connector housing 103 for insertion into a corresponding port on a host device. External connector 105 may comprise, for example, a USB connector (for example USB v1.1 or v2.0), an IEEE 1394 connector, DIN-9 compliant connector, RJ-45 compliant connector, RJ-11 compliant connector, or any other suitable type of connector for insertion into a respective port on, for example, a host device.

In one embodiment, housing 103 comprises width 111 at a widest point of about 0.9 inches, height 113 at a highest point of about 0.9 inches, and length 115 of about 1.53 inches. In addition, inner diameter 107 of socket cavity 102 is, for example, about 0.60 inches, and outer diameter 109 is, for example, about 0.90 inches. One skilled in the art will appreciate that such dimensions, as with the other listings of dimensions throughout this specification, may be modified without departing from the spirit of the invention.

Figure 2:
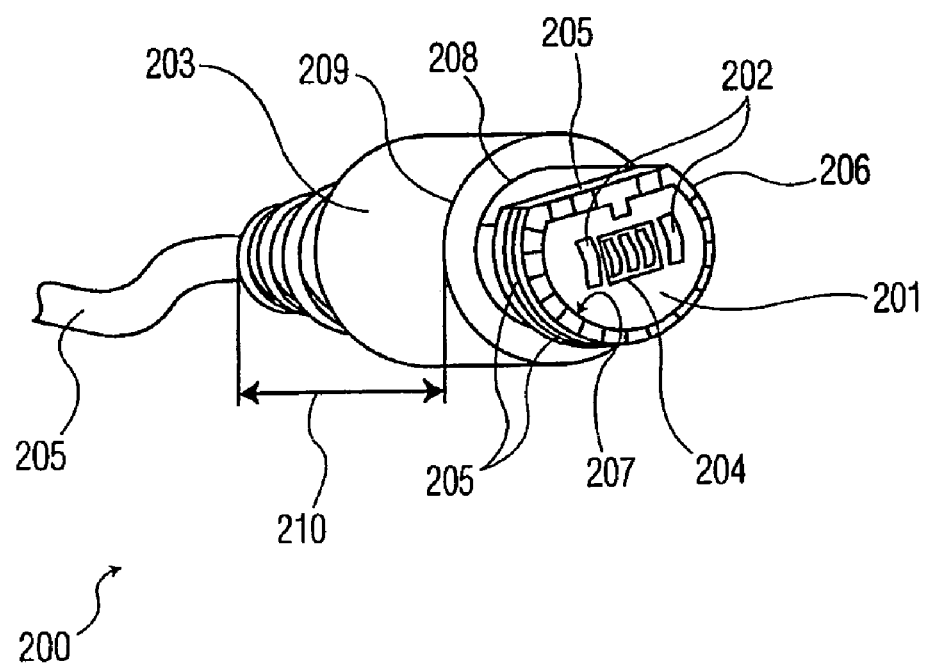
FIG. 2 is a perspective view of a mating plug for connecting with the safety connector according to an embodiment of the present invention.

FIG. 2 depicts an exemplary illustration of mating plug 200 for connection with safety connector 100. Head portion 201 is preferably fixedly attached to plug housing 203. Cable 205 is attached to a second end of plug housing 203 for connection to, for example, a peripheral device.

A shape of the face of head portion 201 is preferably adapted to fit into socket cavity 102. Preferably, the configuration of socket cavity 102 and head portion 201 are designed to ensure proper pin alignment. For example, in one embodiment, the face of head portion 201 comprises a substantially semi-circular shape to ensure proper sequencing of the center pins 106 and outer pins 104 when connected with a corresponding semicircular shaped socket cavity 102. The quick release connector, according to the invention, may also be implemented with connectors having pre-determined connect and disconnect pin configurations. For example, the connection and disconnection of connector pins 104 and 106 in a pre-determined sequence can be effected by varying the depth, staggering the depth, and adjusting the spring force of the connector contacts, or a combination thereof, to ensure that certain contacts are made or broken in a desired sequence. Those of ordinary skill will recognize that the order of that connectors contacts are connect and disconnect sequence of the connector contacts may be modified without departing from the spirit of the invention.

Head portion 201 includes a plurality of plug contacts, for example, plug outer pins 202 and plug center pin assembly 204 for connection with connector outer pins 102 and connector center pin assembly 104, respectively, when head portion 201 is inserted into socket cavity 102. In addition, the head portion 201 comprises conductive shell 205 for providing an electrically conductive means for shielding, for example, electromagnetic interference (EMI) and radio frequency interference (RFI). Conductive shell 205 may be formed of, for example, any type of conductive material (e.g., nickel, silver, gold, copper, nickel beryllium, carbon seeded rubber, conductive metals, etc.). It is to be noted that in one embodiment, a perimeter of conductive shell 205 is greater than a perimeter of a face of head portion 201 (see FIG. 3B).

For example, in one embodiment, outer diameter 206 is about 0.75 inches and inner diameter 207 of a face of head portion 201 is about 0.64 inches. Additionally, inner housing diameter 208 is about 0.60 inches and outer housing diameter 209 is about 0.90 inches. Housing length 210 is about 0.82 inches.

Advantageously, socket 101, according to an aspect of the present invention, provides secure support and gripping of mating plug 200 sufficient to maintain a proper electrical connection between the plurality of electrical contacts on the connector 100 and the electrical contacts on plug 200, while at the same time facilitating easy and immediate release of mating plug 200 in the event of, for example, accidental or unintentional physical interference with plug 200, cable and/or the connector such that a force is applied to separate connector 100 and plug 200 (i.e., someone pulls or trips on the cable 205, the host device and/or peripheral device is accidentally moved, etc.). For example, the separation force is at least 0.10 Newtons, although one in the ordinary skill in the art may modify the minimum force required for separation depending on the requirements necessary for connecting two devices. Socket 101 according to the present invention grips mating plug 200 by, for example, resiliently pressing against head portion 201.

Figure 3B:
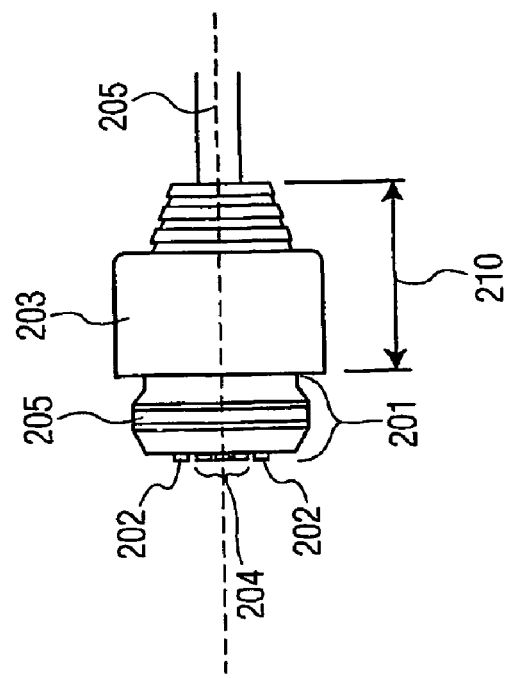
FIG. 3B is a top view of the mating plug of FIG. 2 according to an embodiment of the present invention.
Figure 3A:
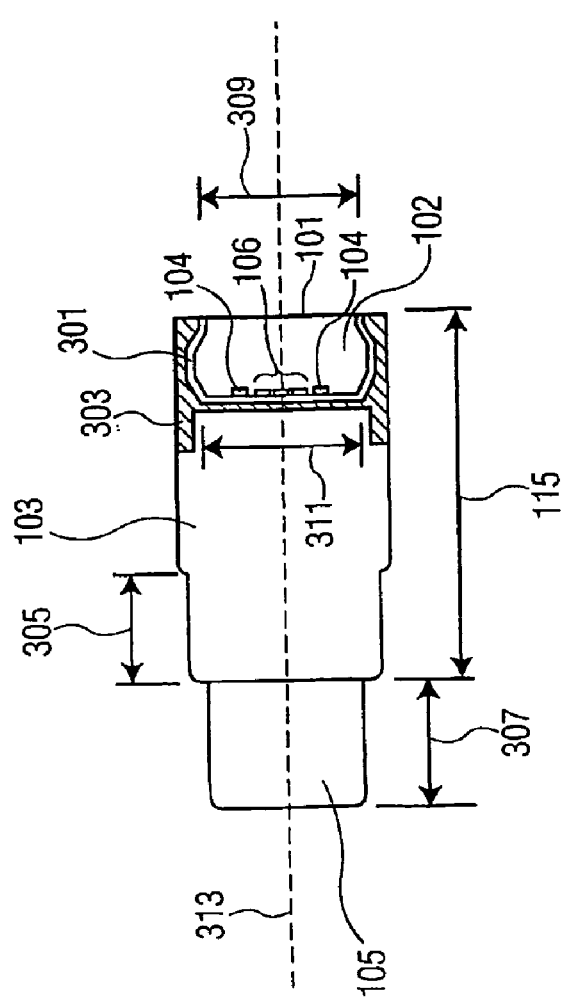
FIG. 3A a top partial cross-sectional view of the safety connector of FIG. 1 according to an embodiment of the present invention.

FIG. 3A depicts an exemplary illustration of a top partial cross-sectional view of safety connector of 100, according to an embodiment of the present invention. Socket 101 preferably comprises a conductive lining 301 for providing an electrically conductive means for shielding against EMI and RFI. Conductive lining 301 is preferably comprised of a resilient conductive material, for example, conductive silicone rubber, rubber seeded with a conductive material (as carbon, gold, silver), or any other conductive elastomeric material.

Exterior 303 of socket 101 is preferably comprised of a non-conductive resilient material, for example, non-conductive silicone rubber to prevent electrocution when handling the socket.

In one embodiment, section length 305 of connector housing 103 is about 0.45 inches, and external connector length 307 is about 0.54 inches.

FIG. 3B is a top view of mating plug 200 according to an embodiment of the present invention. As shown, mating plug 200 is preferably adapted to be mated with socket 101; more specifically, the shape of head portion 201 is preferably adapted to fit inside socket cavity 102 and maintain a proper electrical connection when mated with socket 101 such that, for example, conductive shell 205 makes contact with conductive lining 301 and plug contacts 202 and 204 make contact with connector contacts 104 and 106.

When mated, connector 100 and mating plug 200 are preferably connected along axis 313. It is to be noted that in yet another advantage of the present invention, resilient socket 101 provides for quick release of mating member 200 whether plug 200 is pulled out straight from (i.e., axially to) socket 101, or is pulled at any other angle to socket 101 (i.e., in any non-axial direction from the socket 101).

It should be appreciated, by one skilled in the art, that other types of connectors might be constructed employing the aspects of the present invention. Many electrical devices, as cellular phones, personal desk assistants, and other portable devices that when connected to host devices would benefit from a quick release safety connector. Similarly, other developed input and output devices, when connected a network (for example, a home network utilizing a multimedia communications standard as such HAVI, DENI, or Plug and Play) would benefit from a quick release safety connector. The quick release safety connector apparatus, according to the present invention, not only provides for an immediate and reliable release between connected devices in the event of accidental interference with the connecting cord, but also is simple to install and adaptable to a variety of input and output interface ports, for example, USB ports.

In accordance with principles of the invention, the specification supports an embodiment of the present invention describing an electrical connector assembly comprising a connector having a socket end, the socket end including a socket cavity. A mating plug (member) is also provided having a head portion for insertion into the socket cavity. The socket end is formed of a resilient material for flexibly securing the head portion sufficiently enough to establish an electrical connection between the connector and the mating plug.

According to another supported embodiment of the present invention, a connecting member is provided having a resilient socket end. The resilient socket end includes a plurality of first contacts, a socket cavity, an electrically conductive resilient lining and a non-conductive resilient exterior. In addition, a mating member is provided having a head portion. The head portion includes a plurality of second contacts and an electrically conductive shell. The resilient socket end is adapted for receiving and resiliently pressing against the head portion to provide a secure connection between the two components, while at the same time allowing the head portion to be easily released from the socket cavity in the event of physical interference with at least one of the connecting member, the mating member, and/or a connecting wire.

Although illustrative embodiments of the present invention are described herein with reference to the accompanying drawings, it is to be understood that the invention is not limited to those precise embodiments, and that various other changes and modifications may be affected therein by one skilled in the art without departing from the scope or spirit of the present invention.

The invention claimed is:

1. An electrical connector assembly comprising:
a connector having a socket end having a socket cavity for receiving a mating plug, wherein said socket end is comprised of a resilient material for providing a flexible securing of said mating plug sufficient to establish an electrical connection between said connector and said mating plug, wherein:
interior of said socket end comprises a plurality of electrical contacts to form said electric connection with said mating plug;
said socket end comprises a conductive resilient lining forming a chamber around the contacts and a non-conductive resilient exterior; and
said connector comprises a second end forming an external connector end capable of being inserted into and removed from a host device, wherein said socket end and said second end form a unitary unit.

2. The electrical connector assembly of claim 1, wherein said resilient material comprises silicone rubber.

3. The electrical assembly of claim 1, wherein said mating plug comprises a head portion for insertion into said socket cavity forming said electrical connection.

4. The electrical connector assembly of claim 3, wherein said socket end flexibly secures said mating plug by resiliently pressing against the head portion of the mating plug.

5. The electrical connector assembly of claim 4, wherein said head portion comprises a plurality of plug contacts and a conductive shell.

6. The electrical connector assembly of claim 5, wherein an electrical connection is made when said plug contacts contact said connector contacts and said conductive shell contacts said conductive resilient lining.

7. The electrical connector assembly of claim 5, wherein said head portion further comprises a face having a perimeter, said conductive shell comprising a perimeter that is greater than said face perimeter.

8. The electrical connector assembly of claim 4, wherein said socket end provides for release of said head portion when a separation force is applied between said mating plug and said connector.

9. The electrical connector assembly of claim 8, wherein said socket end provides for easy release of said mating plug when pulled non-axially from said connector.

10. The electrical connector assembly of claim 1, wherein said external connector end comprises at least one of: a USB connector, an IEEE 1394 connector, a DIN-9 compliant connector, a RJ-45 compliant connector, and a RJ-11 compliant connector.

11. An apparatus comprising:
a connecting member-having a resilient socket end, said resilient socket end comprising a plurality of first contacts, a socket cavity, a conductive resilient lining forming a chamber around the contacts and a non-conductive resilient exterior; wherein said resilient socket end is adapted for receiving and resiliently connecting to a mating member forming an electrical connection; and
said connecting member additionally comprising a second end forming an external connector end that is capable of being inserted into and removed from a host device, wherein said resilient socket end and said second end form and unitary unit.

12. The apparatus of claim 11, wherein said resilient socket comprises silicone rubber.

13. The apparatus of claim 11, further comprising:
a mating member having a head portion, said head portion comprising a plurality of second contacts and a conductive shell wherein said resilient socket end connects with said head portion by resiliently pressing against said head portion, whereby said head portion is easily released from said socket cavity when a separating force is applied between said connecting member and said mating member.

14. The apparatus of claim 13, wherein said conductive shell comprises a conductive material of at least one of: silicon rubber; carbon seeded rubber, gold seeded rubber, silver seeded rubber, and conductive seeded rubber.

15. The apparatus of claim 13, wherein an electrical connection is made when the plurality of first contacts contact said plurality of second contacts and the conductive shell contacts the conductive resilient lining.

16. The apparatus of claim 13, wherein said mating member further comprises a tail portion for attachment of a cable for connecting to a peripheral device.

17. The apparatus of claim 13, wherein said plurality of: first contacts and said plurality of second contacts each comprise a center data pin assembly for transmission of data, and outer pins for providing power and grounding.

18. The apparatus of claim 13, wherein said head portion further comprises a face having a perimeter, said conductive shell comprising a perimeter that is greater than said face perimeter.

19. The apparatus of claim 13, wherein the resilient socket provides for easy release of the head portion if the mating member is pulled non-axially from the connecting member.

* * * * *